(12) United States Patent
Yamada

(10) Patent No.: US 11,364,154 B2
(45) Date of Patent: Jun. 21, 2022

(54) ABSORBENT ARTICLE

(71) Applicant: Kikuo Yamada, Shinagawa-ku (JP)

(72) Inventor: Kikuo Yamada, Shinagawa-ku (JP)

( * ) Notice: Subject to any disclaimer, the term of this patent is extended or adjusted under 35 U.S.C. 154(b) by 387 days.

(21) Appl. No.: 16/077,518

(22) PCT Filed: Mar. 16, 2017

(86) PCT No.: PCT/JP2017/010706
§ 371 (c)(1),
(2) Date: Aug. 13, 2018

(87) PCT Pub. No.: WO2017/159798
PCT Pub. Date: Sep. 21, 2017

(65) Prior Publication Data
US 2019/0046362 A1 Feb. 14, 2019

(30) Foreign Application Priority Data

Mar. 18, 2016 (JP) .............................. JP2016-055314
Apr. 14, 2016 (JP) .............................. JP2016-081383

(51) Int. Cl.
*A61F 13/15* (2006.01)
*A61F 13/534* (2006.01)
(Continued)

(52) U.S. Cl.
CPC ........ *A61F 13/15211* (2013.01); *A61F 13/15* (2013.01); *A61F 13/15642* (2013.01);
(Continued)

(58) Field of Classification Search
CPC .... A61F 13/15; A61F 13/15642; A61F 13/47; A61F 13/475; A61F 13/51121;
(Continued)

(56) References Cited

U.S. PATENT DOCUMENTS 2,721,554 A * 10/1955 Curt .................... A61F 13/4755
604/382
4,333,464 A 6/1982 Nakano
(Continued)

FOREIGN PATENT DOCUMENTS

CN 101394872 A 3/2009
EP 039973 * 11/1981 ............. A41B 13/02
(Continued)

OTHER PUBLICATIONS

Extended European Search Report dated Jul. 4, 2019 in European Patent Application No. 17766794.6, 6 pages.
(Continued)

*Primary Examiner* — Jacqueline F Stephens
(74) *Attorney, Agent, or Firm* — Oblon, McClelland, Maier & Neustadt, L.L.P.

(57) ABSTRACT

In order to absorb a small amount of liquid, to prevent an absorbent article from being disintegrated by the absorbed liquid, and to prevent piping of a toilet from being clogged even if the absorbent article is flushed into a flush toilet, the absorbent article includes a pulp layer containing a crushed pulp or fibers mainly containing a crushed pulp, and the pulp layer has a water repellent surface layer portion formed by applying a water repellent agent to at least one surface layer portion.

20 Claims, 10 Drawing Sheets

(51) Int. Cl.
| | |
|---|---|
| *A61F 13/475* | (2006.01) |
| *A61F 13/47* | (2006.01) |
| *D21H 17/13* | (2006.01) |
| *D21H 11/16* | (2006.01) |
| *D21H 17/11* | (2006.01) |
| *D21H 27/30* | (2006.01) |
| *D21H 27/38* | (2006.01) |
| *D21H 15/02* | (2006.01) |
| *A61F 13/511* | (2006.01) |
| *A61F 13/512* | (2006.01) |
| *A61L 15/18* | (2006.01) |
| *A61L 15/20* | (2006.01) |
| *A61L 15/24* | (2006.01) |
| *A61L 15/52* | (2006.01) |
| *A61F 13/51* | (2006.01) |

(52) U.S. Cl.
CPC ............ *A61F 13/47* (2013.01); *A61F 13/475* (2013.01); *A61F 13/5123* (2013.01); *A61F 13/51121* (2013.01); *A61F 13/534* (2013.01); *A61L 15/18* (2013.01); *A61L 15/20* (2013.01); *A61L 15/24* (2013.01); *A61L 15/52* (2013.01); *D21H 11/16* (2013.01); *D21H 15/02* (2013.01); *D21H 17/11* (2013.01); *D21H 17/13* (2013.01); *D21H 27/30* (2013.01); *D21H 27/38* (2013.01); *A61F 2013/15235* (2013.01); *A61F 2013/51019* (2013.01); *A61F 2013/51061* (2013.01); *A61F 2013/51078* (2013.01)

(58) Field of Classification Search
CPC ............... A61F 13/5123; A61F 13/534; A61F 2013/15235; A61F 2013/51019; A61F 2013/51061; A61F 2013/51078; A61L 15/18; A61L 15/20; A61L 15/24; A61L 15/52; D21H 11/16; D21H 11/02; D21H 17/11; D21H 17/13; D21H 17/38
See application file for complete search history.

(56) References Cited

U.S. PATENT DOCUMENTS

| | | | | |
|---|---|---|---|---|
| 5,399,175 | A * | 3/1995 | Glaug | ................ A61F 13/4756 604/358 |
| 6,793,649 | B1 * | 9/2004 | Fujioka | ................ A61F 13/474 604/385.05 |
| 2002/0026167 | A1 * | 2/2002 | Pompa | ................ A61F 13/474 604/378 |
| 2009/0012487 | A1 | 1/2009 | Park | |
| 2011/0004179 | A1 * | 1/2011 | Kurihara | ............... A61F 13/474 604/385.02 |
| 2012/0123378 | A1 | 5/2012 | Kato et al. | |
| 2013/0184665 | A1 | 7/2013 | Kato et al. | |
| 2014/0243771 | A1 * | 8/2014 | Konishi | ................ A61L 15/62 604/364 |

FOREIGN PATENT DOCUMENTS

| | | |
|---|---|---|
| EP | 0 557 677 A1 | 9/1993 |
| EP | 2 431 012 A1 | 3/2012 |
| GB | 2014046 A | 8/1979 |
| JP | 7-504103 A | 5/1995 |
| JP | 2004-154326 A | 6/2004 |
| JP | 2004-230127 A | 8/2004 |
| JP | 2004-344443 A | 12/2004 |
| JP | 2007-14657 A | 1/2007 |
| JP | 2008-125851 A | 6/2008 |
| JP | 2012-130363 A | 7/2012 |
| WO | WO 2012/043851 A1 | 4/2012 |

OTHER PUBLICATIONS

International Search Report dated Jun. 6, 2017, in PCT/JP2017/010706 filed Mar. 16, 2017.

Chinese Office Action dated Sep. 21, 2020, in Chinese Patent Application No. 201780018314.6 (with English Translation).

\* cited by examiner

ABSORBENT ARTICLE

TECHNICAL FIELD

The present invention relates to an absorbent article that absorbs a body fluid such as urine, sweat, blood, or lymph mainly discharged from a human body.

BACKGROUND ART

Along with age, not a few middle-aged people have urination problems. Among the urination problems, many people have a symptom of a small amount of urine leakage, so-called light incontinence. Light incontinence occurs, for example, at the moment when a force is applied, such as when a heavy object is raised or a sneeze is made, or when residual urine leaks out after urination.

Conventionally, a pad for light incontinence (hereinafter simply referred to as "incontinence pad") has been commercially available. Such an incontinence pad is compact and thin because the incontinence pad only needs to deal with a small amount of urine leakage, and is not visible from an outside when being worn. For this reason, a demand for the incontinence pad has increased in recent years.

By the way, in most cases, there is no sanitary box in a private room of a male toilet. When a man goes out, the man has to take a used incontinence pad to a trash can by wrapping the incontinence pad with toilet paper and putting the incontinence pad in a pocket. In the meantime, urine may ooze out from the used incontinence pad to contaminate surroundings, and there are a sanitary problem and a problem of a bad odor. Therefore, there is a demand for flushing an incontinence pad for men into a flush toilet.

In addition to the incontinence pad for men, there has also been a need to flush an absorbent article such as a sanitary napkin, a panty liner, or a disposable diaper into a flush toilet.

Therefore, for example, Patent Literature 1 studies an absorbent article that can be flushed into a toilet after use. Patent Literature 1 discloses a water-disintegrable absorbent article including a liquid permeable surface sheet located on a skin surface side when the absorbent article is worn and a water-disintegrable back sheet located on a non-skin surface side, in which hydrophobic fibers and 40% by mass or less of hydrophilic fibers appear on a surface of the surface sheet on a skin surface side, and hydrophilic fibers and 40% by mass or less of hydrophobic fibers appear on a surface of the surface sheet on a non-skin surface side.

CITATION LIST

Patent Literature

Patent Literature 1: JP 2004-344443 A

SUMMARY OF INVENTION

Technical Problem

However, the above-described absorbent article disclosed in Patent Literature 1 contains hydrophobic fibers in the surface sheet and is not disintegrated immediately even if the absorbent article absorbs liquid when being worn. However, even if the absorbent article is exposed to a large amount of water, it takes a long time before the absorbent article is disintegrated in water. Therefore, in a case where the absorbent article is flushed into a flush toilet, piping of the toilet may be clogged.

An object of the present invention is to provide an absorbent article that absorbs a small amount of liquid, is not disintegrated by the absorbed liquid, and prevents piping of a toilet from being clogged even if the absorbent article is flushed into a flush toilet.

Solution to Problem

An absorbent article according to an embodiment of the present invention includes a pulp layer containing a crushed pulp or fibers mainly containing a crushed pulp, and the pulp layer has a water repellent surface layer portion formed by applying a water repellent agent to one surface layer portion.

Advantageous Effects of Invention

According to the present invention, it is possible to realize an absorbent article that absorbs a small amount of liquid, is not disintegrated by the absorbed liquid, and prevents piping of a toilet from being clogged even if the absorbent article is flushed into a flush toilet.

DESCRIPTION OF EMBODIMENTS

Figure 1:
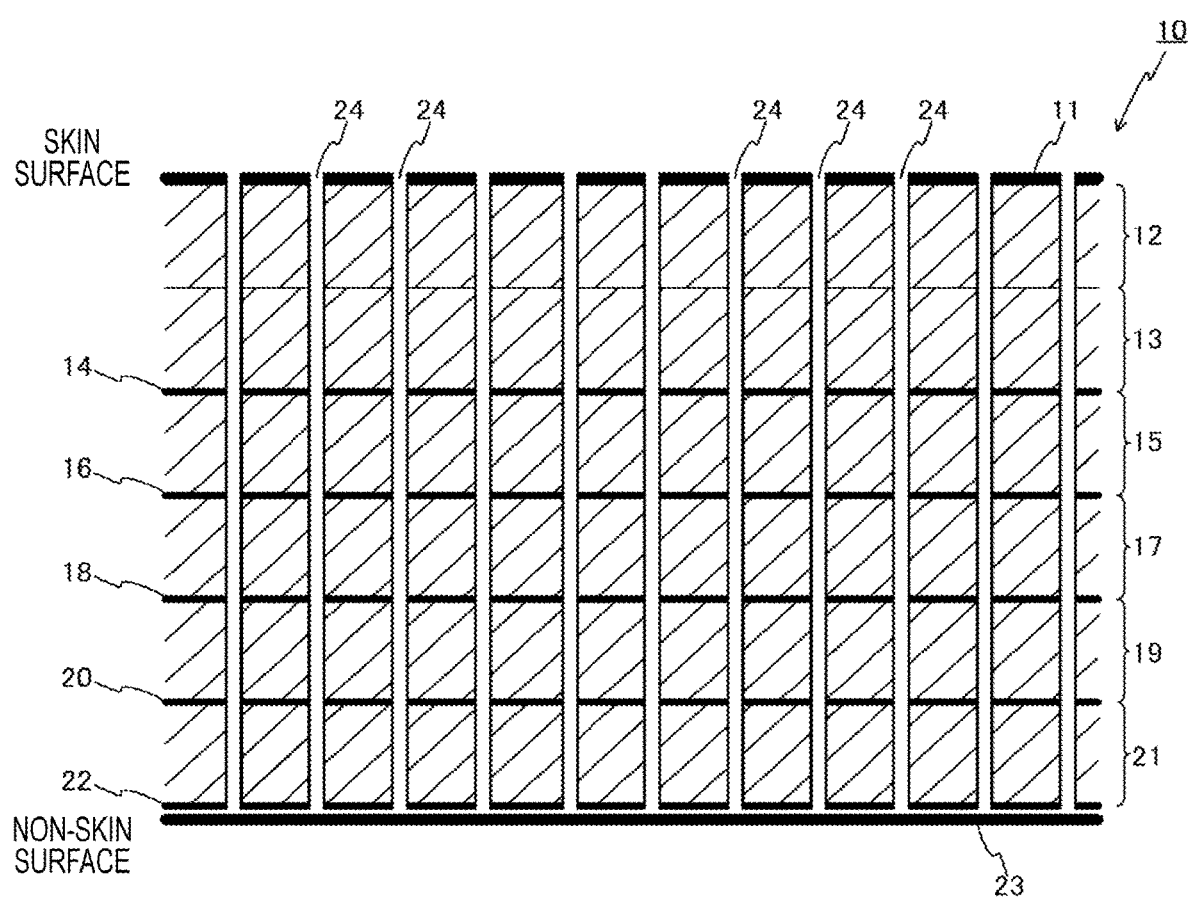
FIG. 1 is a conceptual diagram illustrating a configuration of an absorbent article according to a first embodiment of the present invention.

Hereinafter, embodiments of the present invention will be described with reference to the drawings. However, in the embodiments, the same components are denoted by the same reference numerals, and redundant description is omitted.

First Embodiment

FIG. 1 is a conceptual diagram illustrating a configuration of an absorbent article 10 according to a first embodiment of the present invention. Hereinafter, the absorbent article 10 will be described with reference to FIG. 1. FIG. 1 illustrates a cross section of the absorbent article 10. Hereinafter, the absorbent article 10 will be described assuming an incontinence pad for men as an example.

The absorbent article 10 includes a surface sheet layer 11, a first pulp layer 12, a second pulp layer 13, a third pulp layer 15, a fourth pulp layer 17, a fifth pulp layer 19, and a sixth pulp layer 21 sequentially laminated in order from a skin surface side.

The surface sheet layer 11 is water-disintegrable paper serving as a skin surface when the absorbent article 10 is attached to a human body. Here, "water-disintegrability" refers to a property that entangled fibers are rapidly separated from one another by a water flow having a predetermined flow rate, and each separated element having a size equal to or less than a cross-sectional area of a drain pipe is dispersed in water. Here, for example, if it is assumed that a minimum inner diameter of a drain pipe of a typical house is 5.0 cm, each separated element only needs to have a size of at least about 19.6 cm$^2$ or less. As a result of disintegration in water, most fibers are not bonded by a binder, and a suspended liquid in which fibers and water are mixed with each other is obtained. The amount of water required for disintegration in water is desirably, for example, three times or more the volume of an object to be disintegrated in water.

The surface sheet layer 11 has liquid permeability, and is formed from pulp paper or a material mainly containing a pulp, that is, a material containing a cellulose-based component. In a case where the surface sheet layer 11 is formed from a material mainly containing a pulp, a blending ratio of the pulp is desirably 30% or more. In addition, the blending ratio of the pulp is more desirably 50% or more. Furthermore, the blending ratio of the pulp is still more desirably 80% or more.

By setting the blending ratio of the pulp to the above ratio, it is possible to improve softness of the absorbent article 10 or to improve the production efficiency at the time of manufacture.

In the case where the surface sheet layer 11 is formed from a material mainly containing a pulp, various raw material pulps can be used as the pulp. Examples of the raw material pulps include a wood pulp, a synthetic pulp, a used paper pulp, and a toilet paper material.

As the wood pulp, it is also possible to use a pulp obtained by blending a coniferous tree bleached kraft pulp obtained from a coniferous tree such as red pine, Yezo spruce, Sakhalin fir, Douglas fir, Hemlock, or spruce, and a broad leaf tree bleached kraft pulp obtained from a broad leaf tree such as beech, Quercus, birch, eucalyptus, oak, poplar, or Alder at a predetermined ratio. However, it is desirable to use a raw material pulp containing a coniferous tree bleached kraft pulp from a viewpoint of manufacture.

In addition, as the material of the surface sheet layer 11, a natural fiber is desirably used. Examples of the natural fiber include kenaf, a bamboo fiber, straw, cotton, a cocoon thread, and sugar cane.

Note that the material used for the surface sheet layer 11 is not limited to those described above.

Examples of a method for manufacturing the surface sheet layer 11 include a wet papermaking method for forming a sheet by dispersing fibers of several millimeters in water and making paper from the dispersed fibers with a wire mesh. In addition, the surface sheet layer 11 may be manufactured by a spun lace method. The spun lace method is also called a water flow entanglement method, and is a method for guarding short fibers and arranging the fibers to prepare a web, emitting a jet water flow to the web, and entangling the fibers with one another by water pressure to bond the fibers to one another into a sheet shape.

The surface sheet layer 11 is subjected to water repellent finish by applying a water repellent agent to a surface of the absorbent article 10 serving as a skin surface side when the absorbent article 10 is attached to a human body. The surface of the surface sheet layer 11 to which a water repellent agent has been applied is referred to as a water repellent surface. The water repellent agent and an applying method will be described below.

The first pulp layer 12 is laminated between the surface sheet layer 11 and the second pulp layer 13. The first pulp layer 12 includes a crushed pulp or innumerable fibers mainly containing a crushed pulp. The first pulp layer 12 may be configured such that the degree of clustering of fibers varies in a thickness direction. The first pulp layer 12 is formed by, for example, an air laid method for accumulating a crushed pulp or innumerable fibers mainly containing a crushed pulp along an air flow flowing downward. The first pulp layer 12 thus formed is pressed by a pressing member, and the bulkiness thereof is adjusted. In FIG. 1, the first pulp layer 12 seems to have a considerable thickness because FIG. 1 is a schematic view, but is made thin actually.

Here, the crushed pulp refers to a product obtained by finely crushing a raw material pulp which is a raw material of a paper material with a crusher so as to be a cotton-like pulp. Various raw material pulps can be used as a material of the crushed pulp, and the material of the crushed pulp is similar to the raw material pulp constituting the surface sheet layer 11.

Since the crushed pulp is obtained by crushing a pulp material so as to be a cotton-like pulp, in a case where the cotton-like crushed pulp is accumulated, it is easier to form a space between fibers. Since these spaces are formed innumerably between a fiber and a fiber, the bulkiness of the first pulp layer 12 can be made larger with a smaller basis weight than the surface sheet layer 11 by these formed spaces.

In addition, as described above, by forming the first pulp layer 12 from a cotton-like crushed pulp, it is possible to form a space between fibers to increase the degree of freedom of movement of each fiber and to increase the bulkiness of the first pulp layer 12. This can contribute to improvement in softness of the entire absorbent article 10 and can improve the production efficiency at the time of manufacture.

Since the second pulp layer 13 to the sixth pulp layer 21 are manufactured from similar raw materials and by similar manufacturing methods to those of the first pulp layer 12, detailed description thereof is omitted.

The second pulp layer 13 to the sixth pulp layer 21 are subjected to water repellent finish by applying a water repellent agent to a surface layer portion serving as a non-skin surface side when the absorbent article 10 is attached to a human body. The surface layer portions of the second pulp layer 13 to the sixth pulp layer 21 to which a water repellent agent has been applied are referred to as water repellent surface layer portions 14, 16, 18, 20, and 22, respectively. Each of the surface layer portions includes a surface and a predetermined thickness from the surface. Examples of the water repellent agent include a silicon-based water repellent agent, a fluorine-based water repellent agent, a paraffin-based water repellent agent (wax), vegetable oil, animal oil, and mineral oil. A silicon-based water repellent agent or a fluorine-based water repellent agent is particularly preferable.

Examples of the silicon-based water repellent agent include dimethylpolysiloxane and a modified polysiloxane compound obtained by introducing a hydroxy group, an amino group, an epoxy group, or a polyether group into a molecular terminal or a side chain of dimethylpolysiloxane. Examples of the silicon-based water repellent agent further include a cyclic siloxane such as hexamethylcyclotrisiloxane, octamethylcyclotetrasiloxane, or decamethylcyclopentasiloxane.

Examples of the fluorine-based water repellent agent include polytetrafluoroethylene (PTFE), a tetraethyl ene-hexafluoropropylene copolymer (PFEP), an ethylene-tetrafluoroethylene copolymer (PETFE), a tetrafluoroethylene-perfluoroalkyl vinyl ether copolymer (PFA), an ethylene-chlorotrifluoroethylene copolymer (PECTFE), a tetrafluoroethylene-hexafluoropropylene-perfluoroalkyl vinyl ether copolymer (PEPE), polychlorotrifluoroethylene (PCTFE), polyvinylidene fluoride (PVdF), polyvinyl fluoride (PVF), polyhexafluoropropylene, and fluorinated graphite.

Examples of a method for water repellent finish include application of a water repellent agent by spraying, gravure printing, or flexographic printing. Among these methods, application by spraying is desirable. A reason for this will be described below. Spraying includes one-fluid method and two-fluid method, and the one-fluid method is desirable. Note that the one-fluid method is a method for emitting a water repellent agent compressed by a pump from a nozzle, and the two-fluid method is a method for making two fluids of a compressed water repellent agent and compressed air collide with each other and emitting the fluids.

When the application amount of a water repellent agent is small, disintegration of the absorbent article 10 and urine leakage are caused by a small amount of urine. Conversely, when the application amount of a water repellent agent is large, even if the absorbent article 10 is immersed in a large amount of water, the absorbent article 10 is not disintegrated in water. Therefore, the application amount of a water repellent agent is, for example, in a range of 0.1 to 5.0% by weight, preferably in a range of 1.0 to 3.5% by weight with respect to the second pulp layer 13. The third pulp layer 15 to the sixth pulp layer 21 are also similar to the second pulp layer 13. However, the application amount of a water repellent agent applied to the fifth pulp layer 19 is desirably twice the application amount of the second pulp layer 13. This can further prevent permeation of urine into a non-skin surface. In addition, a skin surface side of the sixth pulp layer 21 may be subjected to water repellent finish. This is also for preventing permeation of urine into a non-skin surface.

A back sheet layer 23 is water-disintegrable paper serving as a non-skin surface when the absorbent article 10 is attached to a human body. Since the back sheet layer 23 is manufactured from similar raw materials and by similar manufacturing methods to those of the surface sheet layer 11, detailed description thereof is omitted.

The back sheet layer 23 is subjected to water repellent finish by applying a water repellent agent to a surface of the absorbent article 10 serving as a non-skin surface when the absorbent article 10 is attached to a human body. The surface of the back sheet layer 23 to which a water repellent agent has been applied is referred to as a water repellent surface. The water repellent agent and an applying method are similar to those described above. However, the application amount of a water repellent agent applied to each of the surface sheet layer 11 and the back sheet layer 23 is desirably about three to four times the application amount to the second pulp layer 13. This makes it possible to prevent urine from returning from the surface sheet layer 11 and to prevent permeation leakage of urine from the back sheet layer 23 to a non-skin surface.

Note that the sixth pulp layer 21 and the back sheet layer 23 may be folded back and joined to the surface sheet layer 11 at an end portion of a laminate including the surface sheet layer 11 to the fifth pulp layer 19.

A hole 24 is a hole penetrating the surface sheet layer 11 to the sixth pulp layer 21. The hole 24 is formed, for example, by causing a cylinder having a diameter of about 3 mm as a bottom surface to penetrate the layers. The holes 24 are formed substantially regularly over the entire surface of the surface sheet layer 11. By forming the holes 24, urine can be absorbed through the holes 24 even if the surface sheet layer 11 is subjected to water repellent finish.

Figure 2:
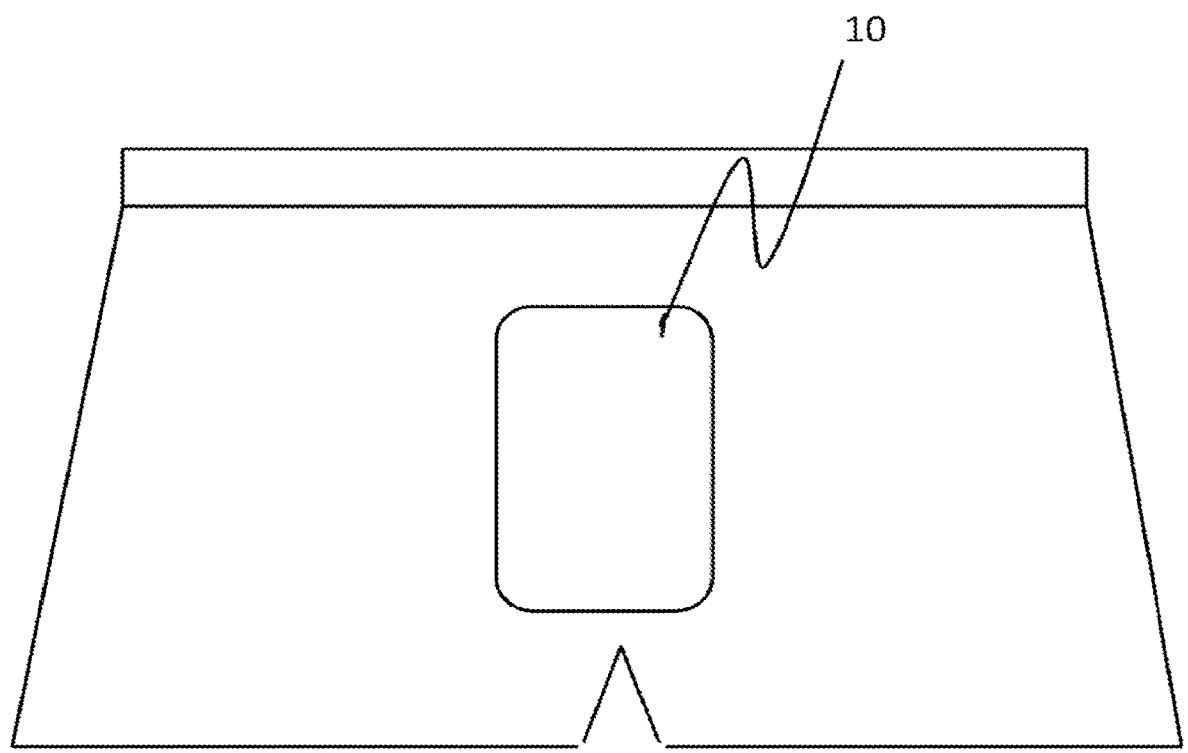
FIG. 2 is a schematic diagram illustrating a state in which an absorbent article is attached to a trunks-type underwear.

FIG. 2 illustrates a state in which the absorbent article 10 is attached to a trunks-type underwear. FIG. 2 illustrates a state in which a front part of the trunks-type underwear is viewed from the inside. Here, since the absorbent article 10 is assumed to be an incontinence pad for men, the absorbent article 10 is disposed in the vicinity of the inner center of the front part.

Incidentally, in a case where the absorbent article 10 is formed from an almost 100% pulp, even if the absorbent article 10 is brought into direct contact with a delicate crotch part of a human body, a skin rash hardly occurs, and the absorbent article 10 is gentle to the skin.

Next, a state in which the absorbent article 10 absorbs a small amount of urine will be described. Here, it is assumed that the absorbent article 10 absorbs about 10 cc of urine.

Urine excreted in the surface sheet layer 11 of the absorbent article 10 is absorbed by the first pulp layer 12 and the second pulp layer 13 through the holes 24 formed in the surface sheet layer 11.

Urine absorbed by the first pulp layer 12 and the second pulp layer 13 is delayed in absorption into the third pulp layer 15 by the water repellent surface layer portion 14 of the second pulp layer 13. In the meantime, the urine is further dispersed throughout the first pulp layer 12 and the second pulp layer 13.

Urine that has passed through the holes 24 reaches the third pulp layer 15 and is absorbed by the third pulp layer 15. In addition, urine that has passed through the water repellent surface layer portion 14 of the second pulp layer 13 is absorbed by the third pulp layer 15. Urine that has reached the third pulp layer 15 is delayed in absorption into the fourth pulp layer 17 by the water repellent surface layer portion 16 of the third pulp layer 15. In the meantime, the urine is further dispersed throughout the third pulp layer 15.

Urine that has passed through the holes 24 reaches the fourth pulp layer 17 and is absorbed by the fourth pulp layer 17. In addition, urine that has passed through the water repellent surface layer portion 16 of the third pulp layer 15 is absorbed by the fourth pulp layer 17. Urine that has reached the fourth pulp layer 17 is delayed in absorption into the fifth pulp layer 19 by the water repellent surface layer portion 18 of the fourth pulp layer 17. In the meantime, the urine is further dispersed throughout the fourth pulp layer 17.

Urine that has passed through the holes 24 reaches the fifth pulp layer 19 and is absorbed by the fifth pulp layer 19. In addition, urine that has passed through the water repellent surface layer portion 18 of the fourth pulp layer 17 is absorbed by the fifth pulp layer 19. Urine that has reached the fifth pulp layer 19 is delayed in absorption into the sixth pulp layer 21 by the water repellent surface layer portion 20 of the fifth pulp layer 19. In the meantime, the urine is further dispersed throughout the fifth pulp layer 19.

Urine that has passed through the holes 24 reaches the sixth pulp layer 21 and is absorbed by the sixth pulp layer 21. In addition, urine that has passed through the water repellent surface layer portion 20 of the fifth pulp layer 19 is absorbed by the sixth pulp layer 21. Urine that has reached the sixth pulp layer 21 is delayed in permeation into a non-skin surface by the water repellent surface layer portion 22 of the sixth pulp layer 21 and a water repellent surface of the back sheet layer 23. In the meantime, the urine is further dispersed throughout the sixth pulp layer 21. The water repellent surface layer portion 22 of the sixth pulp layer 21 and the water repellent surface of the back sheet layer 23 prevent urine absorbed by the sixth pulp layer 21 from permeating a non-skin surface.

As described above, urine moves through the holes 24, and the urine is dispersed throughout each pulp layer. This makes it possible to reduce the amount of urine reaching a non-skin surface through the absorbent article 10 and to prevent an underwear from becoming dirty. In addition, urine absorbed in each pulp layer is prevented from returning by a water repellent surface portion of each pulp layer and a water repellent surface of the surface sheet layer 11. Therefore, it is possible to suppress discomfort and uneasiness of a user.

Next, a state in which the absorbent article 10 is disintegrated in water will be described.

First, if a pulp layer has a high fiber density and does not have a sufficient thickness, a water repellent agent applied to the pulp layer permeates the inside due to a capillary phenomenon. In this case, liquid does not permeate a gap between fibers, and therefore the fibers are not disintegrated in water. In contrast, if a pulp layer has a low fiber density and has a sufficient thickness, a water repellent agent applied to the pulp layer remains in a surface layer portion. In this case, liquid penetrates a gap between fibers. From this fact, a pulp layer desirably has such a thickness that a water repellent agent does not permeate from an applied surface to the opposite surface, for example, when a water repellent agent is applied in a minimum amount that can be controlled by spraying.

Here, when the absorbent article 10 is immersed in an appropriate amount of water, water permeates the first pulp layer 12 to the sixth pulp layer 21, and separates entanglement of fibers constituting these layers. Although having a function of bonding a pulp layer, a water repellent surface layer portion disposed in a pulp layer does not have a very strong bonding force. Therefore, as a pulp layer is disintegrated, fibers bonded to one another by a water repellent agent bond are also separated from one another. As a result, the absorbent article 10 is disintegrated rapidly (for example, within 10 seconds) by an appropriate amount of water. Therefore, even if the absorbent article 10 is flushed into a flush toilet, there is no risk that piping of the toilet will be clogged.

The absorbent article 10 is desirably further subjected to a process for imparting an additional function. For example, at least one of the first pulp layer 12 to the sixth pulp layer 21 of the absorbent article 10 may be impregnated with an agent that exerts various functions, such as a deodorant, a fragrance, an antibacterial agent, or a softener.

A deodorant is desirably added to the absorbent article 10 because the absorbent article 10 absorbs urine. Specific examples of the deodorant include catechin, epigallocatechin, gallocatechin, epicatechin gallate, epigallocatechin gallate, gallotannin, and ellagitannin which are extracts from plants such as catechins or tannins, an iron-ascorbic acid chelate compound, a hydroxide of zirconium, a hydroxide of lanthanoid, and a metal salt of Zn, Cu, Fe, or Ag (for example, $ZnSO_4$). Specific examples of the deodorant further include a deodorant utilizing an adsorption action, and examples thereof include activated carbon, zeolite, silica, ceramic, Oya stone, charcoal polymer, carbon nanotubes, carbon nanohorns, an organic acid such as citric acid or succinic acid, an inorganic acid such as sulfuric acid, boric acid, or phosphoric acid, an ion exchanger, a nucleophilic agent such as an anion, ammonia, an amine, an alkene, an alkyne, or an aromatic compound, and an electrophile such as a cation, boron fluoride, aluminum chloride, iron bromide, zinc chloride, or acetone. These deodorants may be used singly or in combination of two or more kinds thereof. Note that a deodorant applicable to the present invention is not limited to these deodorants.

In addition, as the fragrance, for example, a fruit such as an orange, a lemon, a lime, or a peach, a flower such as rose or lavender, or an essential oil such as mint or sandalwood (vegetation) is preferably selected. Usually, an aroma component is oily or water/alcohol-soluble. Examples of the oily fragrance include phenylethyl alcohol, linalool, jasmone, hexylcinnamic aldehyde, α-limonene, α-pinene, bromostyrol, citronellal, corollal, terpionel, menthol, and cinnamic acid. These fragrances may be used singly or in combination of two or more kinds thereof.

In addition, examples of the antibacterial agent include a carbendazim derivative having antibacterial properties, zinc, copper, iron, silver, gold, and platinum. These antibacterial agents may be used singly or in combination of two or more kinds thereof.

Furthermore, as the softener, a cationic surfactant such as an alkylated quaternary ammonium salt widely used as a rinse agent for hair and a softening agent for clothes is preferably used. Examples thereof include dicocoyl dimethyl ammonium chloride and alkyl trimethyl ammonium chloride. In addition, as the softener, glycerin, propylene glycol, butylene glycol, dipropylene glycol, and liquid paraffin are also preferably used. These softeners may be used singly or in combination of two or more kinds thereof.

Next, an example of a process for manufacturing the absorbent article 10 will be described. The process for manufacturing the absorbent article 10 mainly includes a fiber accumulating step, a pressing step, a water repellent agent applying step, a drying step, a penetration step, and a joining step.

In the fiber accumulating step, a crushed pulp or innumerable fibers mainly containing a crushed pulp are accumulated along an air flow flowing downward by an air laid method to form a pulp layer.

The pressing step presses the pulp layer obtained in the fiber accumulating step. Examples of a pressing member include a pair of flat rolls. At this time, the flat rolls heat the pulp layer desirably at about 50 to 100° C., more desirably at about 60 to 80° C. In the pressing step, the bulkiness of a pulp layer is adjusted by pressing the pulp layer. When a pulp layer is made thin by adjusting the bulkiness of the pulp layer, urine is easily diffused in the pulp layer, and a diffusion speed can be improved.

The water repellent agent applying step is a step following the pressing step, and applies a water repellent to one surface layer portion of the pressed pulp layer. A water repellent agent is desirably applied by spraying. In spraying, it is not possible to control the size (particle size) of a droplet sprayed from a spray. For this reason, droplets having uneven particle sizes are dropped onto a pulp layer. In addition, due to spraying, applying unevenness may occur. From these facts, unevenness in water repellent strength slightly occurs. As a result, for example, the water repellent surface layer portion 14 of the second pulp layer 13 prevents permeation of urine into the third pulp layer 15 in a portion where the water repellent strength is relatively strong, and promotes permeation of urine into the third pulp layer 15 in a portion where the water repellent strength is relatively weak. That is, as a whole, permeation of urine into the third pulp layer 15 can be delayed. The same applies to another pulp layer having a water repellent surface layer portion.

The drying step is a step following the water repellent agent applying step and is not particularly limited, but examples of a drying means include aeration drying (hot air drying), infrared drying, hot roll drying, and electromagnetic wave drying. Even after moisture evaporates, a water repellent agent increases a bonding strength by being heated at a predetermined temperature. That is, the bonding strength of a crushed pulp or fibers mainly containing a crushed pulp, constituting the water repellent surface layer portion, is increased. The predetermined temperature is often higher than 100° C., for example, 160° C. For this reason, air drying (hot air drying), infrared drying, and hot roll drying are desirable. A water repellent agent is heated at a predetermined temperature by either drying to increase the bonding strength.

As described above, the pulp layer having bulkiness adjusted by the pressing step increases the adjusted bulkiness and becomes soft because of being subjected to the water repellent agent applying step and the drying step. As a result, a wearing feeling of a user is favorable.

In the penetration step, first, a laminate in which the surface sheet layer 11 and a plurality of dried pulp layers are laminated is obtained. In the penetration step, a hole penetrating all the layers of the obtained laminate is formed. At this time, for example, a drill or a comb can be used.

In the joining step, as illustrated in FIG. 1, a laminate is obtained in which the surface sheet layer 11 with a hole opened, a plurality of pulp layers, and the back sheet layer 23 are laminated. In the joining step, the resultant laminate is thermally pressure-bonded (heat-sealed), and joining is performed through all the layers of the laminate. Specifically, in the joining step, portions corresponding to end portions (four sides) of the absorbent article 10 are joined by thermal pressure-bonding. Particularly, one side corresponding to a lower end portion of the absorbent article 10 is desirably joined double by thermal pressure-bonding.

After the joining step, a step for cutting the absorbent article 10 may be performed as appropriate.

Incidentally, it may be possible to apply a binder to a pulp layer, dry the binder to fix the pulp layer, and then apply a water repellent agent. In this case, the binder is not particularly limited as long as having a predetermined adhesive force and being able to impart a predetermined strength to the pulp layer, and various binders are used. Examples of the binder include a polysaccharide derivative, a natural polysaccharide, and a synthetic polymer.

Examples of the polysaccharide derivative include carboxymethyl cellulose (CMC), carboxyethyl cellulose, carboxymethylated starch or a salt thereof, starch, methyl cellulose, and ethyl cellulose. Examples of the natural polysaccharide include guar gum, tragacanth gum, xanthan gum, sodium alginate, carrageenan, gum arabic, gelatin, and casein. Examples of the synthetic polymer include polyvinyl alcohol (PVA), an ethylene-vinyl acetate copolymer resin (EVA), a polyvinyl alcohol derivative, a polymer or a copolymer of an unsaturated carboxylic acid, and salts thereof. Examples of the unsaturated carboxylic acid include acrylic acid, methacrylic acid, maleic anhydride, maleic acid, and fumaric acid. Among these compounds, carboxymethyl cellulose (CMC) and polyvinyl alcohol (PVA) are particularly desirable. These binders may be used singly or in combination of two or more kinds thereof.

Note that a crosslinking agent may be used to improve the physical strength of a binder. The crosslinking agent is a chemical agent to cause a crosslinking reaction with a binder to make the binder to have a crosslinked structure. As the crosslinking agent, in a case where a binder having a carboxyl group, such as carboxym ethyl cellulose (CMC), is used, a polyvalent metal ion is desirably used. Examples of the polyvalent metal ion include metal ions of zinc, an alkaline earth metal, manganese, nickel, and cobalt. Specifically, ions of zinc, calcium, barium, cobalt, and nickel are preferably used. These ions are desirable in imparting a sufficient wet strength. The polyvalent metal ions are used in a form of a water-soluble metal salt such as a sulfate, a chloride, a hydroxide, a carbonate, or a nitrate.

As described above, the absorbent article 10 of the first embodiment is obtained by laminating the first pulp layer 12 to the sixth pulp layer 21 having the water repellent surface layer portions 14 to 22 obtained by applying a water repellent agent to surface layer portions on a non-skin surface side with the first pulp layer 12 to the sixth pulp layer 21 sandwiched between the surface sheet layer 11 and the back sheet layer 23, and holes 24 penetrating the surface sheet layer 11 to the sixth pulp layer 21 are formed at regular intervals. As a result, linear penetration of urine absorbed by a skin surface into a non-skin surface is suppressed, and urine is sequentially and efficiently dispersed in each pulp layer. Therefore, even if the absorbent article 10 absorbs a small amount of urine, the absorbent article 10 is not disintegrated, and it is possible to reduce the amount of urine reaching the non-skin surface through the absorbent article 10, to prevent an underwear from becoming dirty, and to suppress discomfort and uneasiness of a user. Meanwhile, if the absorbent article 10 is immersed in an appropriate amount of water, the absorbent article 10 can be rapidly disintegrated, and even if the absorbent article 10 is flushed into a toilet, piping of the toilet is not clogged.

Incidentally, according to the description of the present embodiment, the holes 24 penetrate the surface sheet layer 11 to the sixth pulp layer 21, but the present invention is not limited thereto. For example, the holes 24 only need to penetrate any part of the surface sheet layer 11 to the sixth pulp layer 21, and the lengths of the plurality of holes 24 may be different from one another.

Second Embodiment

Figure 3:
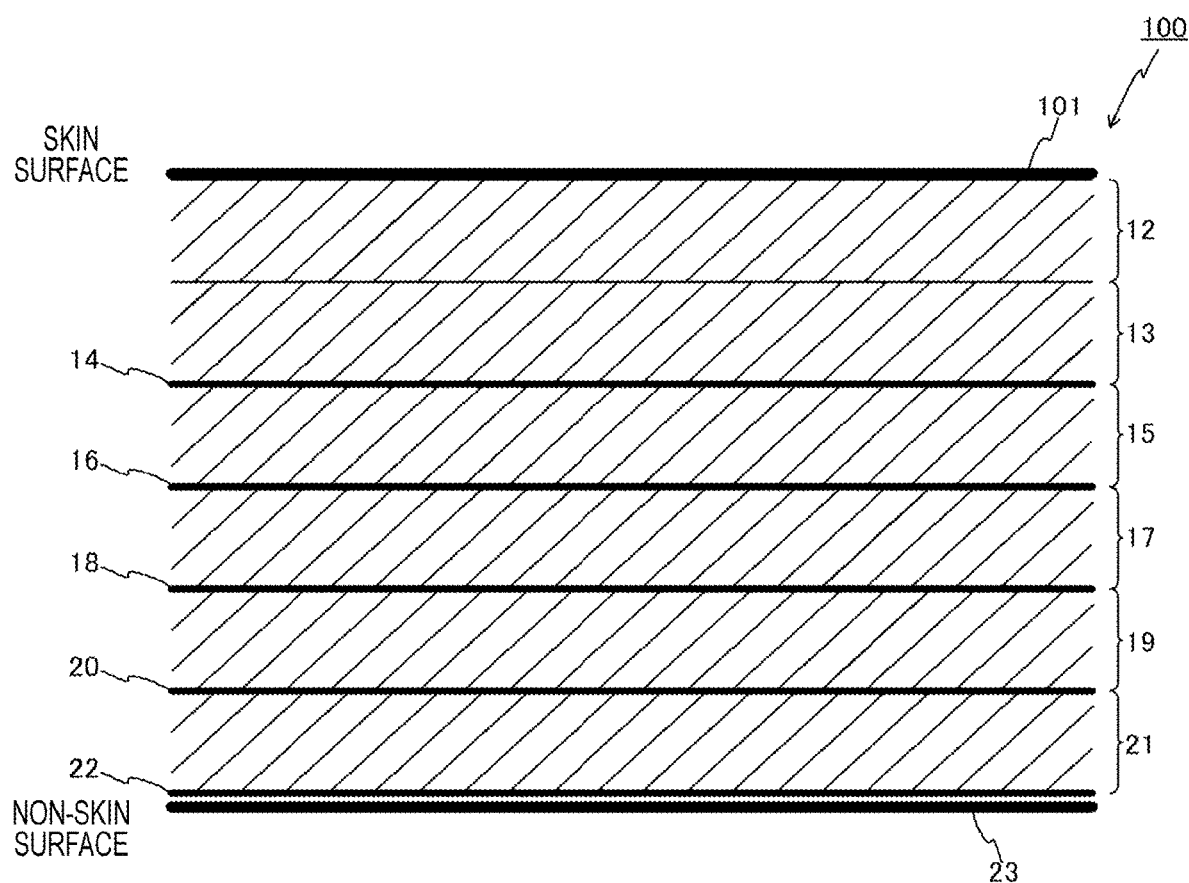
FIG. 3 is a conceptual diagram illustrating a configuration of an absorbent article according to a second embodiment of the present invention.

FIG. 3 is a conceptual diagram illustrating a configuration of an absorbent article 100 according to a second embodiment of the present invention. FIG. 3 is different from FIG. 1 in that the surface sheet layer 11 is changed to a surface sheet layer 101, and the holes 24 are eliminated.

The surface sheet layer 101 is different from the surface sheet layer 11 in that the surface sheet layer 101 is embossed and a water repellent agent is not applied to the surface sheet layer 101, and is similar to the surface sheet layer 11 in the other points.

In the absorbent article 100, at least the surface sheet layer 101 is embossed, and a regular shape is imparted. Note that embossing may be applied to any one or all of a first pulp layer 12 to a sixth pulp layer 21 and a back sheet layer 23.

As an embossed pattern formed on the surface sheet layer 101, for example, embossed patterns illustrated in FIGS. 4(a) to 4(h) are conceivable. Each of FIGS. 4(a) to 4(h) illustrates a skin surface side of the surface sheet layer 101. Upper, lower, left, and right directions when the absorbent article 100 is attached to a human body are defined conveniently as illustrated in the figure.

FIG. 4(a) illustrates a plurality of patterns arranged obliquely from the top to the bottom toward the left and right sides from the center line side of the surface sheet layer 101 in the vertical direction. In the pattern illustrated in FIG. 4(a), urine discharged from a human body is pulled by gravity and moves downward, and also moves to both the left and right sides along the embossed pattern. As a result, urine is dispersed throughout the surface sheet layer 101, and urine can be prevented from concentrating in one place. Therefore, it is possible to suppress permeation of urine into a non-skin surface of the absorbent article 100.

FIG. 4(b) is a pattern obtained by rotating the pattern of FIG. 4(a) by 180°. Specifically, FIG. 4(b) illustrates a plurality of patterns arranged obliquely from the bottom to the top toward the left and right from the center line side of the surface sheet layer 11 in the vertical direction. In the pattern illustrated in FIG. 4(b), urine discharged from a human body moves along the embossed pattern toward the center line of the absorbent article 100 in the vertical direction. This can prevent urine from leaking from both the left and right sides.

FIG. 4(c) illustrates a pattern in which a plurality of round shapes is arranged. However, the round shape may be circular, elliptical, or annular. In the pattern illustrated in FIG. 4(c), since urine moves between embossed portions, the urine is dispersed throughout the surface sheet layer 101 and can be prevented from concentrating in one place.

FIG. 4(d) illustrates a pattern in which two sets of elliptical arcs having two different sizes are arranged line-symmetrically with respect to the center line extending in the vertical direction. Note that the elliptical arcs may be curves. In the pattern illustrated in FIG. 4(d), urine spreads and moves from an upper part of the absorbent article 100 to a lower part via the center along the embossed pattern. This can prevent urine from leaking from both the left and right sides.

FIG. 4(e) illustrates a pattern in which a plurality of L-shaped bent portions is arranged upward on the center line of the surface sheet layer 101 extending in the vertical direction. In the pattern illustrated in FIG. 4(e), urine is pulled by gravity and moves downward, and also moves to both the left and right sides along the embossed pattern. As a result, urine is dispersed throughout the surface sheet layer 101, and urine can be prevented from concentrating in one place. Therefore, it is possible to suppress permeation of urine into a non-skin surface of the absorbent article 100.

FIG. 4(f) is a pattern obtained by rotating the pattern of FIG. 4(e) by 180°. Specifically, FIG. 4(f) illustrates a pattern in which a plurality of L-shaped bent portions is arranged downward on the center line of the surface sheet layer extending in the vertical direction. In the pattern illustrated in FIG. 4(f), urine moves along the embossed pattern toward the center line of the absorbent article 100 extending in the vertical direction. This can prevent urine from leaking from both the left and right sides.

FIGS. 4(g) and 4(h) illustrate lattice-shaped patterns. Incidentally, the embossed patterns illustrated in FIGS. 4(a) to 4(h) may be arbitrarily combined with one another.

As described above, by embossing the surface sheet layer 101, in addition to the above effects, transpiration is improved, and the contact area to the skin can be reduced. Therefore, stuffiness hardly occurs, a sticking feeling to the skin is suppressed, and a comfortable wearing feeling is obtained. In addition, by embossing, air easily passes through the surface sheet layer 101, and therefore air permeability is improved. Furthermore, since a sound of paper slippage can be reduced, there is no risk that surrounding people are aware of wearing of the absorbent article 100.

Note that the four side end portions of the absorbent article 100 are joined by an ultrasonic wave or thermal pressure-bonding. Particularly, as illustrated in FIGS. 4(a) to 4(h), one side end portion located at a lower part is desirably joined double by an ultrasonic wave or thermal pressure-bonding. As a result, urine moving downward can be stopped more reliably, and urine leakage can be prevented. Joining in the absorbent article 100 may be performed by an ultrasonic wave or thermal pressure-bonding, but is more desirably performed by thermal pressure-bonding.

Next, a state in which the absorbent article 100 absorbs a small amount of urine will be described. Here, it is assumed that the absorbent article 100 absorbs about 10 cc of urine.

Urine excreted in the surface sheet layer 101 of the absorbent article 100 moves along an embossed shape formed in the surface sheet layer 101, and is absorbed by the first pulp layer 12 and the second pulp layer 13 on a non-skin surface side through the surface sheet layer 101 to which a water repellent agent is not applied.

Urine absorbed by the first pulp layer 12 and the second pulp layer 13 is delayed in absorption into the third pulp layer 15 by the water repellent surface layer portion 14 of the second pulp layer 13. In the meantime, the urine is further dispersed throughout the first pulp layer 12 and the second pulp layer 13.

The urine that has passed through the water repellent surface layer portion 14 of the second pulp layer 13 is absorbed by the third pulp layer 15. Urine that has reached the third pulp layer 15 is delayed in absorption into the fourth pulp layer 17 by the water repellent surface layer portion 16 of the third pulp layer 15. In the meantime, the urine is further dispersed throughout the third pulp layer 15.

As described above, the urine can sequentially reach the sixth pulp layer 21.

Next, an example of a process for manufacturing the absorbent article 100 will be described. The process for manufacturing the absorbent article 100 mainly includes a fiber accumulating step, a first pressing step, a water repellent agent applying step, a drying step, a second pressing step, and a joining step. The process for manufacturing the absorbent article 100 is different from the process for manufacturing the absorbent article 10 of the first embodiment in that the penetration step is eliminated and the second pressing step is added. However, the first pressing step corresponds to the pressing step of the first embodiment. Therefore, different points from the process for manufacturing the absorbent article 10 will be described below.

In the second pressing step, a pressing member presses at least the surface sheet layer 101. By performing a pressing treatment using, for example, a pair of embossing rolls as the pressing member, an embossed shape including many uneven bodies is formed on the surface sheet layer 101. The pair of embossing rolls may be a combination of a protruding roll and a recessed roll, or a combination of a protruding roll and a flat roll. Examples of the embossed pattern include those illustrated in FIGS. 4(a) to 4(h). Note that it is only required to perform the pressing treatment using the embossing rolls at least on the surface sheet layer 101, and the pressing treatment may be performed on another pulp layer and the back sheet layer 23.

As described above, the absorbent article 100 of the second embodiment is obtained by laminating the first pulp layer 12 to the sixth pulp layer 21 having water repellent surface layer portions 14 to 22 obtained by applying a water repellent agent to surface layer portions on a non-skin surface side with the first pulp layer 12 to the sixth pulp layer 21 sandwiched between the surface sheet layer 101 and the back sheet layer 23, and at least the surface sheet layer 101 has an embossed shape. As a result, linear penetration of urine absorbed from a skin surface into a non-skin surface is suppressed, and urine is sequentially and efficiently dispersed in each pulp layer. Therefore, even if the absorbent article 100 absorbs a small amount of urine, the absorbent article 100 is not disintegrated, and it is possible to reduce the amount of urine reaching the non-skin surface through the absorbent article 100, to prevent an underwear from becoming dirty, and to suppress discomfort and uneasiness of a user. Meanwhile, if the absorbent article 100 is immersed in an appropriate amount of water, the absorbent article 100 can be rapidly disintegrated, and even if the absorbent article 100 is flushed into a toilet, piping of the toilet is not clogged.

Note that the embossed pattern described in the present embodiment may be combined with the first embodiment as appropriate.

Third Embodiment

Figure 5:
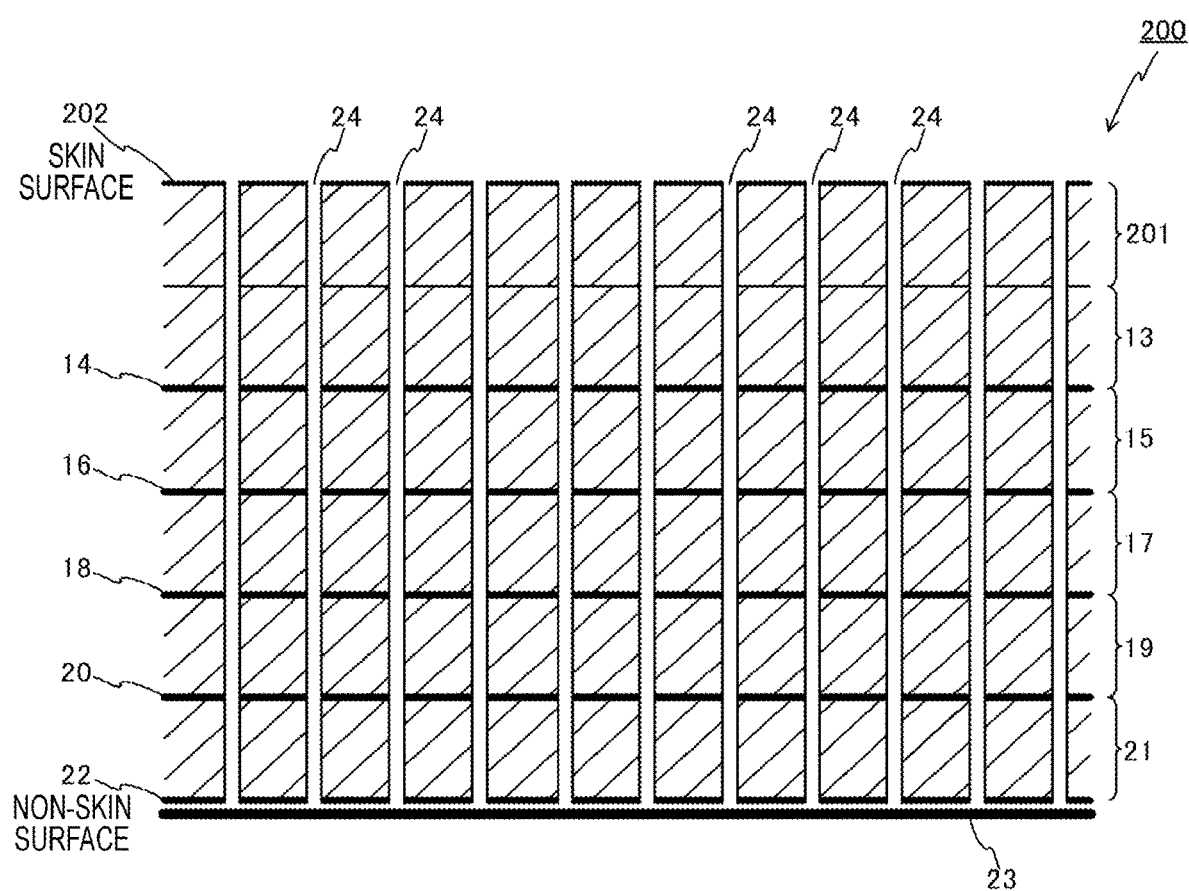
FIG. 5 is a conceptual diagram illustrating a configuration of an absorbent article according to a third embodiment of the present invention.

FIG. 5 is a conceptual diagram illustrating a configuration of an absorbent article 200 according to a third embodiment of the present invention. FIG. 5 is different from FIG. 1 in that the first pulp layer 12 is changed to a first pulp layer 201, and the surface sheet layer 11 is eliminated.

The first pulp layer 201 is subjected to water repellent finish by applying a water repellent agent to a surface layer portion serving as a skin surface when the absorbent article 200 is attached to a human body. The surface layer portion of the first pulp layer 201 to which a water repellent agent has been applied is referred to as a water repellent surface layer portion 202. The first pulp layer 201 is similar to the first pulp layer 12 in the other points.

As described above, since the surface layer portion of the first pulp layer 201 is a skin surface, when the absorbent article 200 is worn, the soft surface layer portion of the first pulp layer 201 comes into contact with the skin, and a wearing feeling is favorable. In addition, by subjecting the surface layer portion of the first pulp layer 201 to water repellent finish, fibers of the pulp are solidified to prevent dissipation of paper powder. In addition, by subjecting the surface layer portion to water repellent finish, urine can be efficiently absorbed from holes 24.

As described above, the absorbent article 200 of the third embodiment forms a skin surface in contact with a human body into the first pulp layer 201 which has been subjected to water repellent finish with a water repellent agent. This can improve a wearing feeling when the absorbent article 200 is attached to a human body, to prevent absorbed urine from returning back, to prevent dissipation of paper powder, and to efficiently absorb urine from the holes 24.

Note that the embossed pattern described in the second embodiment may be combined with the present third embodiment as appropriate.

Fourth Embodiment

Figure 6:
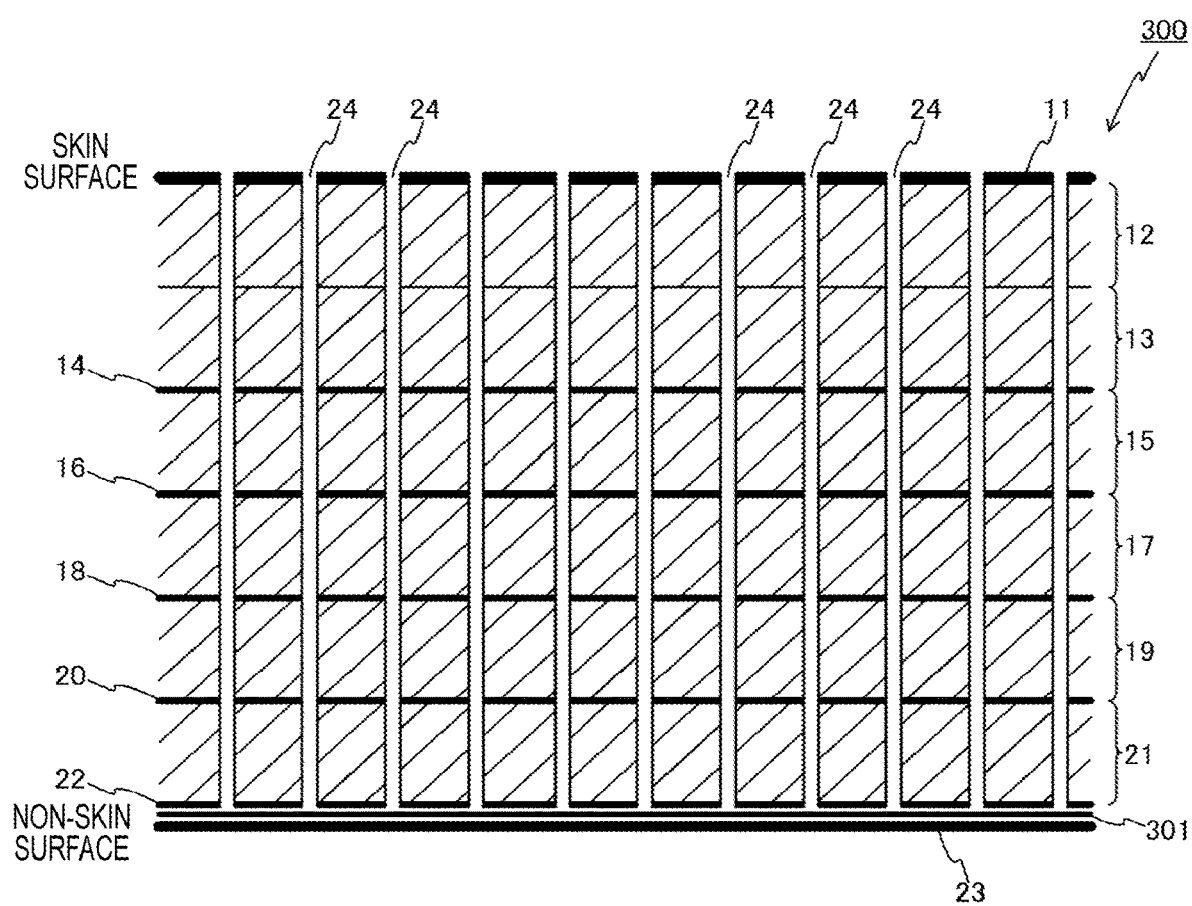
FIG. 6 is a conceptual diagram illustrating a configuration of an absorbent article according to a fourth embodiment of the present invention.

FIG. 6 is a conceptual diagram illustrating a configuration of an absorbent article 300 according to a fourth embodiment of the present invention. FIG. 6 is different from FIG. 1 in that a waterproof sheet layer 301 is added.

The waterproof sheet layer 301 is a water-soluble film sheet and is laminated between a sixth pulp layer 21 and a back sheet layer 23. The waterproof sheet layer 301 prevents urine absorbed by the sixth pulp layer 21 from permeating the back sheet layer 23. The waterproof sheet layer 301 is not disintegrated for a predetermined time even when coming into contact with water and is disintegrated after the predetermined time. In addition, the waterproof sheet layer 301 is disintegrated in a shorter time as the thickness of the sheet is smaller, and is disintegrated in a longer time as the thickness of the sheet is larger. Note that the waterproof sheet layer 301 can be joined to a pulp layer and the back sheet layer 23 by thermal pressure-bonding or with an adhesive.

As described above, by disposing the waterproof sheet layer 301 between the sixth pulp layer 21 and the back sheet layer 23, permeation leakage of urine into a non-skin surface can be prevented. In addition, this makes it possible to omit any one or more pulp layers among a first pulp layer 12 to the sixth pulp layer 21, and to make the absorbent article 300 thin.

As described above, according to the fourth embodiment, by disposing the water-soluble waterproof sheet layer 301 between the sixth pulp layer 21 and the back sheet layer 23, permeation leakage of urine into a non-skin surface can be prevented.

Incidentally, according to the description of the present embodiment, the waterproof sheet layer 301 is disposed between the sixth pulp layer 21 and the back sheet layer 23, but the present invention is not limited thereto. For example, the waterproof sheet layer 301 may be disposed at any position between the surface sheet layer 11 and the back sheet layer 23, or may be disposed on a side closer to a non-skin surface than the back sheet layer 23. In addition, instead of the back sheet layer 23, the waterproof sheet layer 301 may be disposed.

Incidentally, according to the description of the first to fourth embodiments, an absorbent includes the back sheet layer 23, but the present invention is not limited thereto. That is, an absorbent article does not need to include the back sheet layer 23. In a case where an absorbent article does not include the back sheet layer 23, a non-skin surface of the absorbent article is the sixth pulp layer 21. A surface layer portion of the sixth pulp layer 21 on the side opposite to the fifth pulp layer 19 (a surface layer portion not facing the fifth pulp layer 19) is subjected to water repellent finish by applying a water repellent agent thereto.

The water repellent finished water repellent surface layer portion 22 of the sixth pulp layer 21 serving as a non-skin surface can be said to be a coarse surface with fibers of a pulp exposed. Therefore, when the absorbent article is worn, the non-skin surface of the absorbent article comes into contact with an underwear, and a large resistance generated between the underwear and the absorbent article can prevent slippage of the absorbent article. In addition, by embossing the water repellent surface layer portion 22 and imparting an embossed shape, it is possible to further increase a frictional force generated between the absorbent article and the underwear.

Incidentally, in a case where the sixth pulp layer 21 is formed by an air laid method, a gradient (sparse/dense) of a fiber density is generated in a thickness direction of the sixth pulp layer 21. Therefore, a surface layer portion having a low fiber density desirably serves as a non-skin surface.

Incidentally, according to the description of the first to fourth embodiments, the application amount of a water repellent agent applied to a surface layer portion serving as a non-skin surface is the same among the second pulp layer 13 to the fourth pulp layer 17 and the sixth pulp layer 21, and the application amount of a water repellent agent applied to the fifth pulp layer 19 is twice the application amount of the second pulp layer, but the present invention is not limited thereto. For example, a water repellent agent may be applied in a larger amount or a smaller amount to a pulp layer further apart from a skin surface.

According to the description of the first to fourth embodiments, six pulp layers are laminated, but the present invention is not limited thereto. For example, one to five pulp layers having bulkiness adjusted by pressing and having a surface layer portion on a non-skin surface side subjected to water repellent finish may be used, or seven or more layers may be laminated.

Fifth Embodiment

Figure 7:
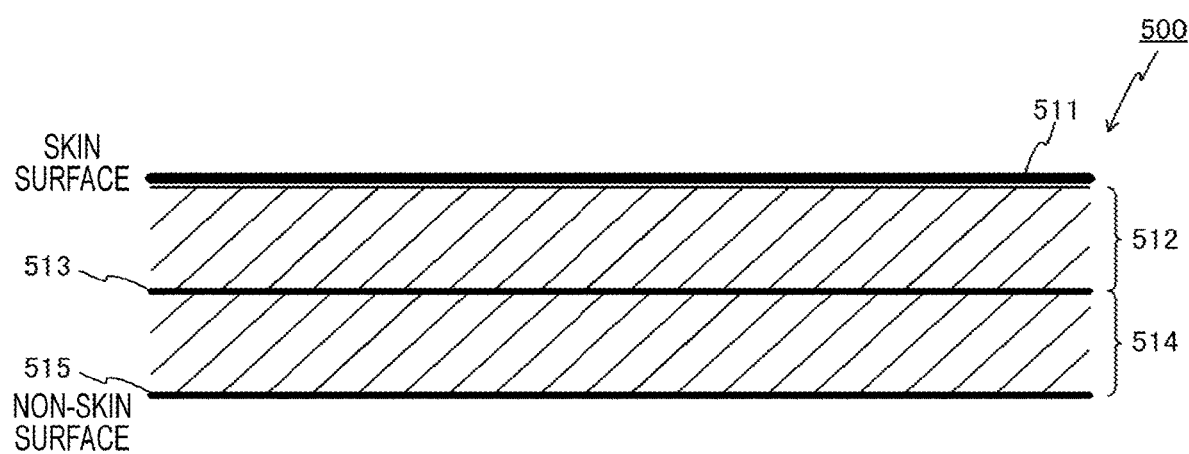
FIG. 7 is a conceptual diagram illustrating a configuration of an absorbent article according to a fifth embodiment of the present invention.

FIG. 7 is a conceptual diagram illustrating a configuration of an absorbent article 500 according to a fifth embodiment of the present invention. Hereinafter, the absorbent article 500 will be described with reference to FIG. 7.

The absorbent article 500 includes a surface sheet layer 511, a first pulp layer 512, and a second pulp layer 514 sequentially laminated in order from a skin surface side.

The surface sheet layer 511 is similar to the surface sheet layer 101 of the second embodiment. That is, the surface sheet layer 511 is different from the surface sheet layer 11 of the first embodiment in that the surface sheet layer 511 is embossed and a water repellent agent is not applied, and is similar to the surface sheet layer 11 in the other points.

The first pulp layer 512 is laminated between the surface sheet layer 511 and the second pulp layer 514 The first pulp layer 512 is similar to the second pulp layer 13 of the first embodiment. Therefore, in the first pulp layer 512, a surface layer portion serving as a non-skin surface side when the absorbent article 10 is subjected to water repellent finish by applying a water repellent agent thereto. Note that a method of water repellent finish is similar to the method of water repellent finish on the second pulp layer 13 to the sixth pulp layer 21 of the first embodiment.

The second pulp layer 514 is disposed on a side closest to a non-skin surface when the absorbent article 500 is attached to a human body. The second pulp layer 514 has a similar configuration to the first pulp layer 512. However, water repellent finish applied to the second pulp layer 514 is performed more firmly than water repellent finish applied to the first pulp layer 512. That is, the application amount of a water repellent agent applied to the second pulp layer 514 is larger than the amount applied to the first pulp layer 512. Note that a method of water repellent finish is similar to the method of water repellent finish on the first pulp layer 512 (the method of water repellent finish on the second pulp layer 13 to the sixth pulp layer 21 of the first embodiment).

In the absorbent article 500, at least the surface sheet layer 511 on a skin surface side is embossed, and a regular shape is imparted thereto. As an embossed pattern formed on the surface sheet layer 511, for example, embossed patterns illustrated in FIGS. 4(a) to 4(h) are conceivable as in the second embodiment.

As described above, by embossing the surface sheet layer 511, transpiration can be improved, and the contact area to the skin can be reduced as in the second embodiment. As a result, stuffiness hardly occurs, a sticking feeling to the skin is suppressed, and a comfortable wearing feeling is obtained. In addition, by embossing, air easily passes through the surface sheet layer 511, and therefore air permeability is improved. Furthermore, since a sound of paper slippage can be reduced, there is no risk that surrounding people are aware of wearing of the absorbent article 500.

In addition, the non-skin surface of the absorbent article 500 is a surface layer portion of the second pulp layer 514 (water repellent surface layer portion 515) which has been subjected to water repellent finish, and can be said to be a coarse surface with fibers of pulp exposed. Therefore, when the absorbent article 500 is worn, the non-skin surface of the absorbent article 500 comes into contact with an underwear, and a large resistance generated between the underwear and the absorbent article 500 can prevent slippage of the absorbent article 500. In particular, by embossing the water repellent surface layer portion 515 and imparting an embossed shape thereto, it is possible to further increase a frictional force generated between the absorbent article 500 and the underwear.

Incidentally, in a case where the second pulp layer 514 is formed by an air laid method, a gradient (sparse/dense) of a fiber density is generated in a thickness direction of the second pulp layer 514. Therefore, a surface layer portion having a low fiber density desirably serves as the water repellent surface layer portion 515.

The absorbent article 500 is desirably subjected to a process for imparting additional functions as in the first to fourth embodiments. For example, the absorbent article 500, particularly the first pulp layer 512 and the second pulp layer 514 may be impregnated with an agent that exerts various functions, such as a deodorant, a fragrance, an antibacterial agent, or a softener. Specific examples of the deodorant, the fragrance, the antibacterial agent, and the softener are similar to those in the first to fourth embodiments.

Next, a state in which the absorbent article 500 absorbs a small amount of liquid will be described. Here, it is assumed that the absorbent article 500 absorbs about 10 cc of urine.

Urine excreted in the surface sheet layer 511 of the absorbent article 500 moves along an embossed shape formed in the surface sheet layer 511, and is absorbed by the first pulp layer 512 on a non-skin surface side. Urine absorbed by the first pulp layer 512 is delayed in absorption into the second pulp layer 514 by the water repellent surface layer portion 513 of the first pulp layer 512. In the meantime, the urine is further dispersed throughout the first pulp layer 512. Since the water repellent surface layer portion 515 of the second pulp layer 514 is more water repellent than the water repellent surface layer portion 513 of the first pulp layer 512, permeation of urine absorbed by the second pulp layer 514 into a non-skin surface is prevented in the water repellent surface layer portion 515 of the second pulp layer 514.

Note that a state in which the absorbent article 500 is disintegrated in water is similar to that of the first embodiment, and therefore description thereof will be omitted.

Next, an example of a process for manufacturing the absorbent article 500 will be described. The process for manufacturing the absorbent article 500 mainly includes a water repellent agent applying step, a drying step, a pressing step, and a joining step.

The water repellent agent applying step applies a water repellent agent to one surface layer portion of a pulp layer obtained by fiber accumulation by an air laid method. A water repellent agent is desirably applied by spraying. In spraying, it is not possible to control the size (particle size) of a droplet sprayed from a spray. For this reason, droplets having uneven particle sizes are dropped onto a pulp layer. In addition, due to spraying, applying unevenness may occur. From these facts, unevenness in water repellent strength slightly occurs. As a result, the water repellent surface layer portion 513 of the first pulp layer 512 prevents permeation of liquid into the second pulp layer 514 in a portion where the water repellent strength is relatively strong, and promotes permeation of liquid into the second pulp layer 514 in a portion where the water repellent strength is relatively weak. That is, as a whole, permeation of liquid into the second pulp layer 514 can be delayed.

In addition, the water repellent agent applying step applies a water repellent agent in a larger amount to a pulp layer further apart from the surface sheet layer 511. Therefore, the amount of a water repellent agent applied to the second pulp layer 514 is larger than that of the water repellent agent applied to the first pulp layer 512, and the second pulp layer 514 can prevent permeation of liquid into a non-skin surface.

Figure 8:
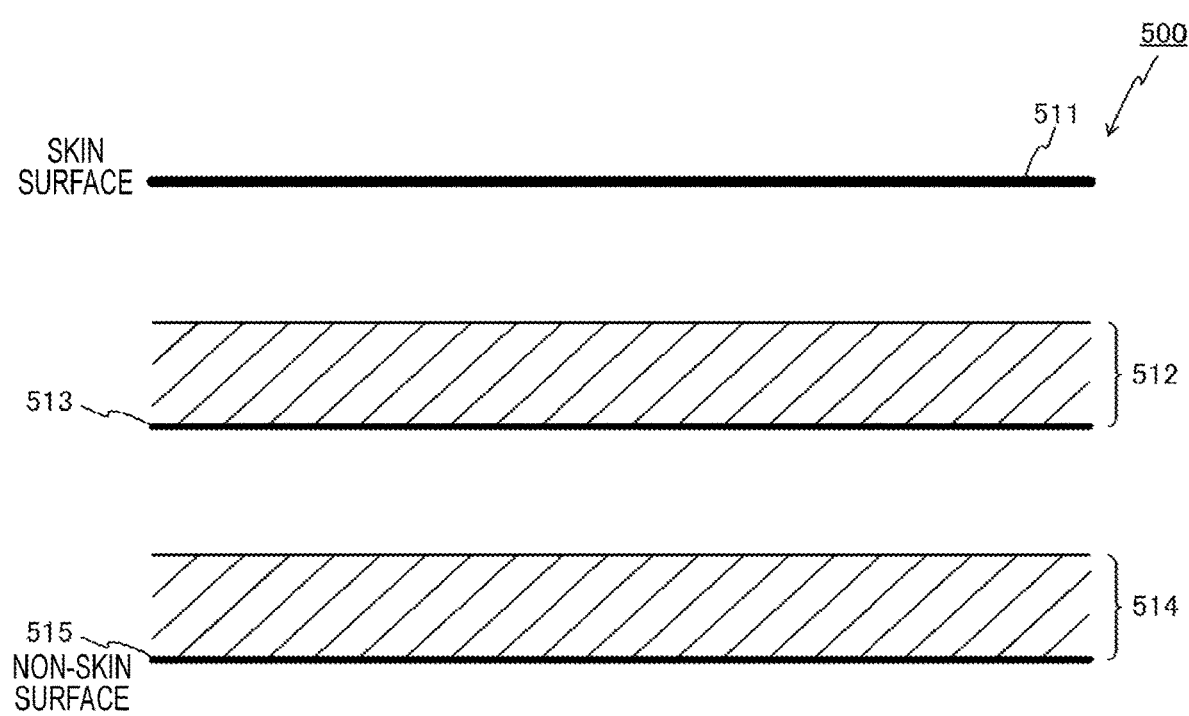
FIG. 8 is a conceptual diagram illustrating a state of the absorbent article of FIG. 7 before lamination.

The drying step is similar to the drying step described in the first embodiment. As illustrated in FIG. 8, the pressing step obtains a laminate obtained by laminating the surface sheet layer 511, and the first pulp layer 512 and the second pulp layer 514 in which a water repellent agent is applied to surface layer portions on a non-skin surface side. In the pressing step, a pressing member presses the laminate. An embossing roll used as the pressing member is similar to that described in the second embodiment. The joining step is similar to the joining step described in the first embodiment.

After the joining step, a step for cutting the absorbent article 500 may be performed as appropriate.

Note that the present invention is not limited to the above manufacturing process, but the following process may be used. For example, a crushed pulp is accumulated on the surface sheet layer 511 to form the first pulp layer 512, and a water repellent is applied to the formed first pulp layer 512, and dried to form the water repellent surface layer portion 513. A crushed pulp is further accumulated on the water repellent surface layer portion 513 to form the second pulp layer 514, and a water repellent agent is applied to the formed second pulp layer 514, and dried to form the water repellent surface layer portion 515.

Incidentally, it may be possible to apply a binder to a pulp layer, dry the binder to fix the pulp layer, and then apply a water repellent agent. In this case, the binder is not particularly limited as long as having a predetermined adhesive force and being able to impart a predetermined strength to the pulp layer, and various binders are used. Examples of the binder include a polysaccharide derivative, a natural polysaccharide, and a synthetic polymer. A crosslinking agent may be used to improve the physical strength of a binder. Note that specific examples of the polysaccharide derivative, the natural polysaccharide, the synthetic polymer, and the binder are similar to those in the first embodiment, and therefore description thereof will be omitted.

As described above, in the absorbent article 500 of the present embodiment, the water-disintegrable surface sheet layer 511, and the first pulp layer 512 and the second pulp layer 514 made of a cotton-like crushed pulp are laminated, and a water repellent agent is applied to surface layer portions of the first pulp layer 512 and the second pulp layer 514 on a non-skin surface side to form the water repellent surface layer portions 513 and 515. As a result, the absorbent article 500 suppresses permeation of liquid absorbed from a skin surface into the non-skin surface, and the liquid is dispersed in the first pulp layer 512 and the second pulp layer 514. Therefore, the absorbent article 500 is not disintegrated even if absorbing a small amount of liquid. Meanwhile, if the absorbent article 500 is immersed in an appropriate amount of water, the absorbent article 500 can be rapidly disintegrated, and even if the absorbent article 500 is flushed into a toilet, piping of the toilet is not clogged.

Here, as a simple experiment for confirming water-disintegrability of the absorbent article 500, the following was performed.

(1) To the surface layer portions of the first pulp layer and the second pulp layer, 0.5% by weight of a water repellent agent (mainly containing silicon, alcohol, and a surfactant) relative to each pulp layer was applied by spraying.

(2) The first pulp layer and the second pulp layer to which the water repellent agent had been applied were heated at 130° C. for two minutes and then heated at 160° C. for one minute.

(3) The absorbent article 500 using the first pulp layer and the second pulp layer obtained by performing the treatments (1) and (2) was prepared so as to have a size of 15 cm×15 cm×0.5 cm.

(4) Into a cylindrical container having a diameter of 17 cm and a height of 14 cm, 300 ml of water was put, and the absorbent article 500 of (3) was immersed therein.

(5) The cylindrical container prepared in (4) was shaken strongly up and down. At this time, one vertical reciprocation was assumed to be one time, and shaking was performed three times.

As a result, the absorbent article 500 was separated into fiber pieces, and suspended liquid was obtained. As a result, it was confirmed that the absorbent article 500 was rapidly disintegrated in water.

Sixth Embodiment

Figure 9:
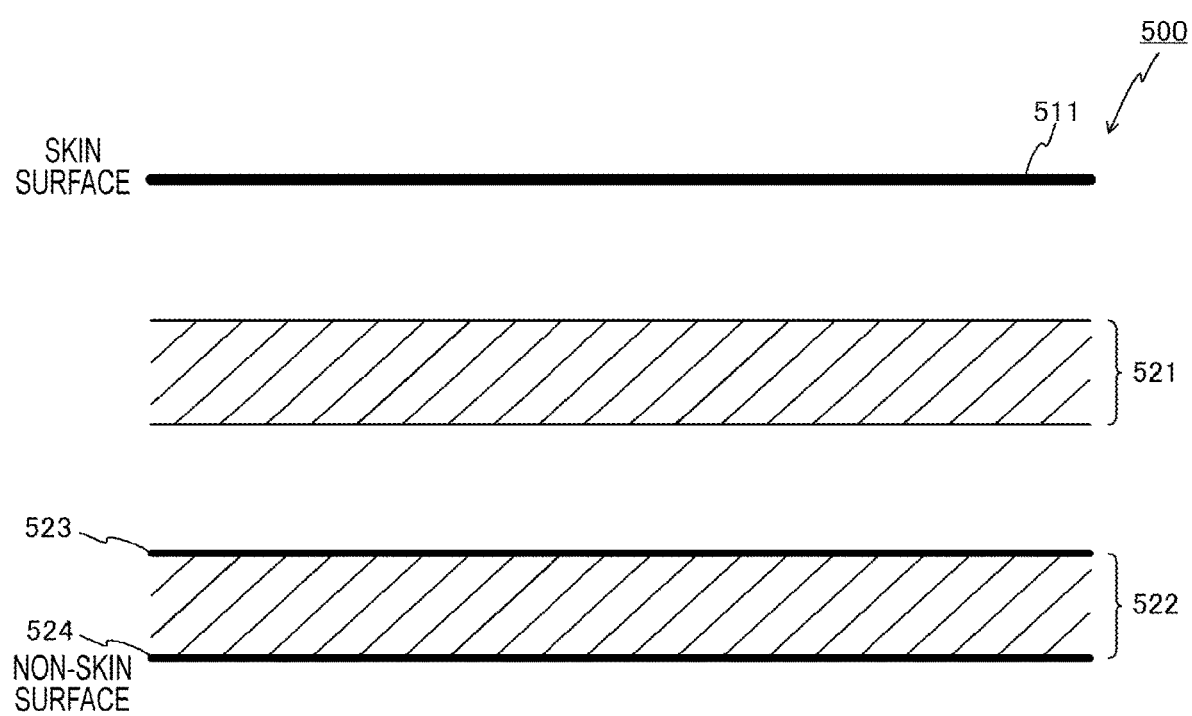
FIG. 9 is a conceptual diagram illustrating another state of the absorbent article of FIG. 7 before lamination.

The present sixth embodiment is different from the fifth embodiment in a state of an absorbent article 500 before lamination. FIG. 9 is a conceptual diagram illustrating a state of the absorbent article 500 before lamination in the present sixth embodiment. In the present sixth embodiment, a water repellent agent is not applied to a first pulp layer 521, but a water repellent agent is applied to surface layer portions of both on a skin surface side and on a non-skin surface side in the second pulp layer 522. At this time, a water repellent agent is applied to the water repellent surface layer portion 524 on the non-skin surface side in a larger amount than to the water repellent surface layer portion 523 on the skin surface side.

By laminating these first pulp layer 521 and second pulp layer 522 and a surface sheet layer 511 and subjecting the laminate to a pressing treatment and a joining treatment, the absorbent article 500 can be formed.

Incidentally, according to the description of the fifth and sixth embodiments, the application amount of a water repellent agent applied to the second pulp layer 514 is larger than the amount applied to the first pulp layer 512, but the present invention is not limited thereto. That is, the application amount of a water repellent agent applied to the second pulp layer 514 may be about the same as or less than the amount applied to the first pulp layer 512.

Figure 10:
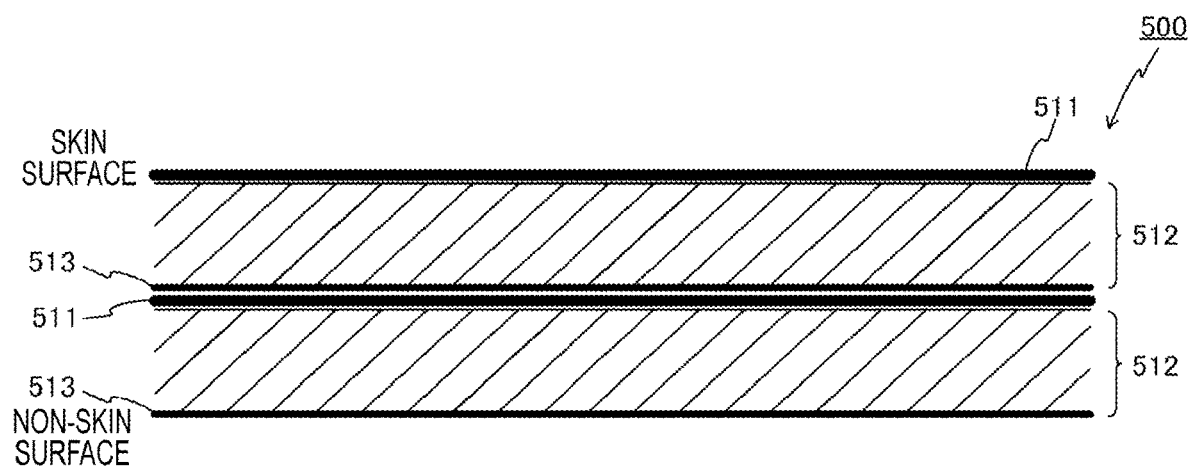
FIG. 10 is a conceptual diagram illustrating an absorbent article according to a sixth embodiment.

According to the description of the fifth and sixth embodiments, the absorbent article 500 is formed by laminating the surface sheet layer 511, the first pulp layer 512, and the second pulp layer 514, but the present invention is not limited thereto. For example, as illustrated in FIG. 10, the absorbent article may be a laminate obtained by laminating two laminates each of which is obtained by laminating the surface sheet layer 511 and the first pulp layer 512. In this case, the surface sheet layer 511, the first pulp layer 512, the surface sheet layer 511, and the first pulp layer 512 are laminated in this order. By adopting such a configuration, it is possible to manufacture the absorbent article more simply.

According to the description of the fifth and sixth embodiments, two pulp layers are laminated, but the present invention is not limited thereto. That is, one pulp layer having a surface layer portion on a non-skin surface side subjected to water repellent finish may be used, or three or more layers may be laminated.

In a case where three or more pulp layers are laminated, a water repellent agent may be applied in a larger amount to apply stronger water repellent finish as a distance from a skin surface increases. This can prevent absorbed liquid from permeating a non-skin surface. However, it is not absolutely necessary to apply a water repellent agent in a larger amount as a distance from a skin surface increases.

In a case where a plurality of pulp layers is laminated, at least one of the pulp layers only needs to be subjected to water repellent finish. That is, in a pulp layer directly or indirectly joined to the surface sheet layer 511, a surface layer portion is subjected to water repellent finish.

According to the description of the fifth and sixth embodiments, the absorbent article 500 includes a surface sheet layer. However, the present invention is not limited thereto, but the absorbent article does not necessarily include the surface sheet layer. In a case where the absorbent article 500 includes no surface sheet layer, a pulp layer is located on a skin surface side, and a surface layer portion of the pulp layer on the skin surface side is embossed.

According to the description of the above embodiments, the surface sheet layer is water-disintegrable. However, the present invention is not limited thereto, but the surface sheet layer may be non-water-disintegrable. Since the surface sheet layer has only a small thickness and a small volume, there is little risk that piping will be clogged even if the surface sheet layer is not disintegrated in water.

Figure 4:
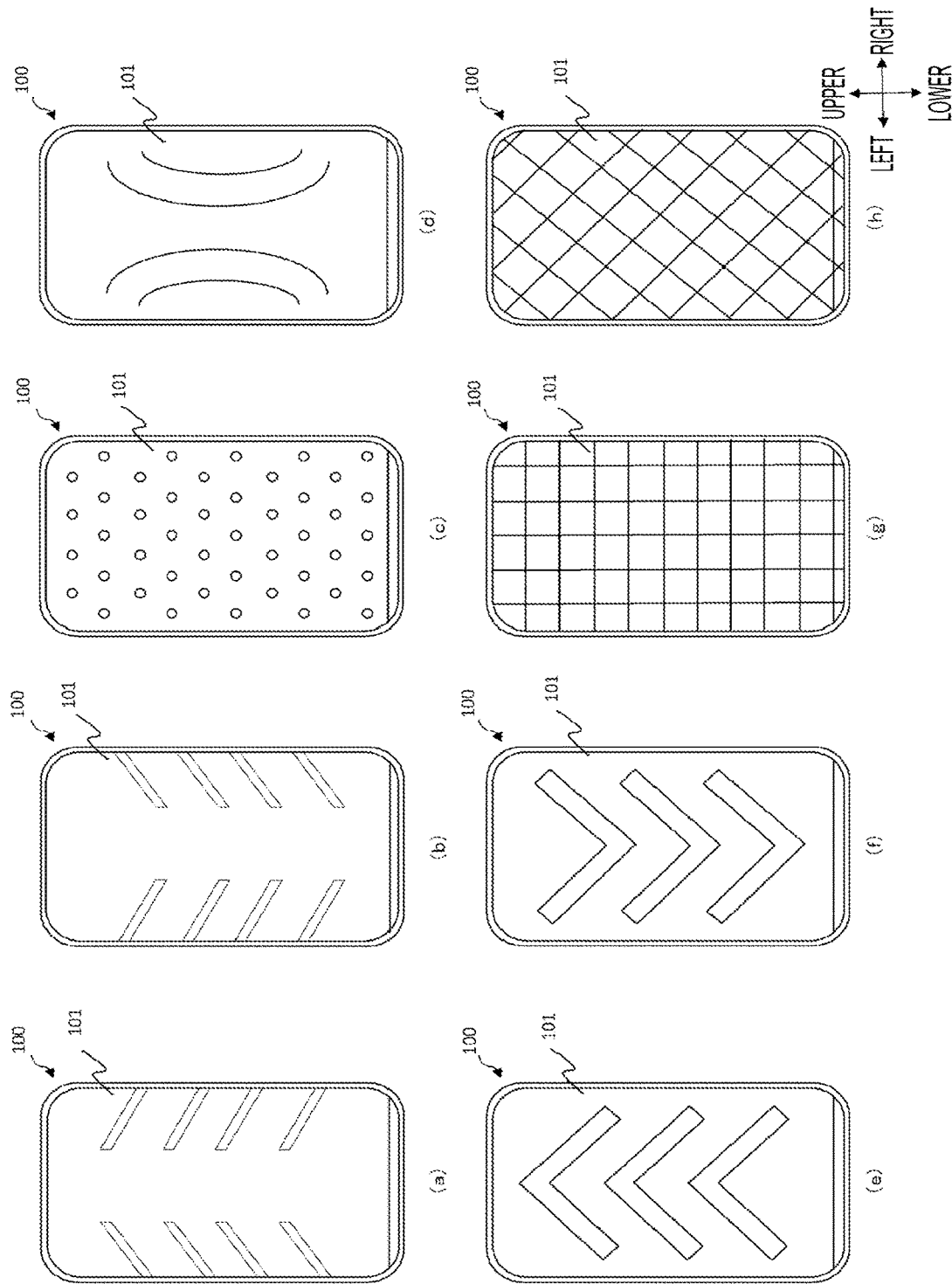
FIGS. 4(a) to 4(h) are diagrams illustrating embossed patterns.

In the above embodiments, when the surface sheet layer and the pulp layer are disposed such that the directions of the eyes of the surface sheet layer and the pulp layer are in a longitudinal direction (vertical direction) in FIG. 4, the tensile strength in the longitudinal direction is improved.

According to the description of the above embodiments, male incontinence is assumed. However, the present invention is not limited thereto. By adjusting an attachment position of the absorbent article, the absorbent article can also deal with female incontinence. That is, the absorbent article can be used for both males and females. In addition, the absorbent article is applicable not only to incontinence, but also to various uses, for example, vaginal discharge, excretion through an artificial anus, or hemorrhoids.

The above-described embodiments are preferable examples of the present invention. However, the present invention is not limited thereto, and various modifications can be made without departing from the gist of the present invention.

REFERENCE SIGNS LIST 10, 100, 200, 500 Absorbent article
11, 101, 511 Surface sheet layer
12, 201, 512, 521 First pulp layer
13, 514, 522 Second pulp layer
15 Third pulp layer
17 Fourth pulp layer
19 Fifth pulp layer
21 Sixth pulp layer
14, 16, 18, 20, 22, 202, 513, 515, 523, 524 Water repellent surface layer portion
23 Back sheet layer
24 Hole

The invention claimed is:

1. An absorbent article, comprising:
a plurality of pulp layers each containing a crushed pulp or fibers mainly containing a crushed pulp, wherein
each of the pulp layers has a water repellent surface layer portion formed by applying a water repellent agent to at least one surface layer portion such that the water repellent surface layer portion has a non-uniform water repellent strength by the water repellent agent, and
the absorbent article has a skin surface and a non-skin surface opposite with respect to the skin surface.

2. The absorbent article according to claim 1, further comprising:
a water-disintegrable sheet layer joined to the plurality of pulp layers.

3. The absorbent article according to claim 1, wherein the water repellent agent is a silicon-based compound or a fluorine-based compound.

4. The absorbent article according to claim 1, wherein the plurality of pulp layers is formed such that an amount of the applied water repellent agent increases from a pulp layer located on a skin surface side toward a pulp layer located on a non-skin surface side.

5. The absorbent article according to claim 1, having an embossed shape on the skin surface.

6. The absorbent article according to claim 1, wherein the water repellent surface layer portion is formed on a non-skin surface side of each of the pulp layers.

7. The absorbent article according to claim 1, wherein the plurality of pulp layers is pressed.

8. The absorbent article according to claim 7, further comprising a water-disintegrable sheet layer joined to an outermost side of the plurality of pulp layers.

9. The absorbent article according to claim 8, wherein the water-disintegrable sheet layer has a water repellent surface formed by applying a water repellent agent.

10. The absorbent article according to claim 8, comprising a hole penetrating the water-disintegrable sheet layer and a part of the plurality of pulp layers.

11. The absorbent article according to claim 10, wherein the absorbent article has a plurality of the holes formed at substantially regular intervals.

12. The absorbent article according to claim 10, wherein the absorbent article has a plurality of the holes, and lengths of the holes are different from one another.

13. The absorbent article according to claim 1, wherein the pulp layers are laminated in a direction from the skin surface to the non-skin surface, and the water repellent surface layer portion is formed on a skin surface side and/or a non-skin surface side of each of the pulp layers.

14. The absorbent article according to claim 1, further comprising a water-disintegrable sheet layer joined to an outermost side of the plurality of pulp layers.

15. The absorbent article according to claim 14, wherein the water-disintegrable sheet layer has a water repellent surface formed by applying a water repellent agent.

16. The absorbent article according to claim 14, comprising a hole penetrating the water-disintegrable sheet layer and a part of the plurality of pulp layers.

17. The absorbent article according to claim 16, wherein the absorbent article has a plurality of the holes formed at substantially regular intervals.

18. The absorbent article according to claim 16, wherein the absorbent article has a plurality of the holes, and lengths of the holes are different from one another.

19. An absorbent article, comprising:
a plurality of pulp layers each containing a crushed pulp or fibers mainly containing a crushed pulp, wherein
each of the pulp layers has a water repellent surface layer portion formed by applying a water repellent agent to at least one surface layer portion,
the absorbent article has a skin surface and a non-skin surface opposite with respect to the skin surface, and
the plurality of pulp layers is formed such that an amount of the applied water repellent agent increases from a pulp layer located on a skin surface side toward a pulp layer located on a non-skin surface side.

20. The absorbent article according to claim 19, wherein the water repellent surface layer portion has a non-uniform water repellent strength by the water repellent agent.

\* \* \* \* \*